United States Patent
Llorente Alonso et al.

(10) Patent No.: US 12,264,844 B2
(45) Date of Patent: Apr. 1, 2025

(54) AIR PURIFICATION DEVICE

(71) Applicant: ZOBELE HOLDING SPA, Trento (IT)

(72) Inventors: Joaquim Llorente Alonso, Barcelona (ES); Moises Caballero Tapia, Barcelona (ES); Alba Graus Ferrer, Barcelona (ES)

(73) Assignee: ZOBELE HOLDING SPA, Trento (IT)

( * ) Notice: Subject to any disclaimer, the term of this patent is extended or adjusted under 35 U.S.C. 154(b) by 910 days.

(21) Appl. No.: 16/972,092

(22) PCT Filed: Jun. 7, 2019

(86) PCT No.: PCT/EP2019/064973
§ 371 (c)(1),
(2) Date: Dec. 4, 2020

(87) PCT Pub. No.: WO2019/234230
PCT Pub. Date: Dec. 12, 2019

(65) Prior Publication Data
US 2021/0222896 A1    Jul. 22, 2021

(30) Foreign Application Priority Data

Jun. 7, 2018 (ES) ................................ P201830555

(51) Int. Cl.
*F24F 8/10* (2021.01)
*A61L 9/12* (2006.01)
*F24F 13/28* (2006.01)

(52) U.S. Cl.
CPC .............. *F24F 8/10* (2021.01); *A61L 9/122* (2013.01); *F24F 13/28* (2013.01);
(Continued)

(58) Field of Classification Search
None
See application file for complete search history.

(56) References Cited

U.S. PATENT DOCUMENTS 9,474,818 B1 * 10/2016 Shotey .................... A61L 9/122
11,739,959 B2 * 8/2023 Park ....................... F24F 1/035
55/283

(Continued)

FOREIGN PATENT DOCUMENTS

EP      2105148 A1 *  9/2009  .......... A01M 1/2033
KR  200303497 Y1 *  2/2003
(Continued)

OTHER PUBLICATIONS

Some FOR documents provided as NPL.*
PCT International Search Report dated Aug. 19, 2019 in connection with PCT/EP2019064973.

*Primary Examiner* — Brit E. Anbacht
(74) *Attorney, Agent, or Firm* — Amster, Rothstein & Ebenstein LLP

(57) ABSTRACT

The invention relates to an air purification device comprising a casing (1) that houses a fan (2) and a filter (3) placed in front of said fan (2), such that air passes through said filter (3) and exits the casing (1) by means of said fan (2), and is characterised in that said filter (3) is placed in a replaceable part (4) mounted in a detachable way in said casing (1), said replaceable part (4) comprising material with volatile substances (5). It allows an air purification device to be provided which allows for the purification of air and the diffusion of volatile substances at the same time.

11 Claims, 3 Drawing Sheets

(52) U.S. Cl.
CPC ...... *A61L 2209/111* (2013.01); *A61L 2209/12* (2013.01); *A61L 2209/133* (2013.01); *A61L 2209/14* (2013.01)

(56) References Cited

U.S. PATENT DOCUMENTS

| | | | | |
|---|---|---|---|---|
| 11,766,027 | B1* | 9/2023 | Ng | A01K 23/005 294/1.3 |
| 2014/0369896 | A1* | 12/2014 | Franks | A61L 9/122 422/124 |
| 2017/0000300 | A1* | 1/2017 | Zheng | A47K 10/48 |
| 2017/0087500 | A1* | 3/2017 | Combs | B01D 46/429 |
| 2017/0151362 | A1* | 6/2017 | Edwards | B65D 25/04 |
| 2018/0154036 | A1* | 6/2018 | Davis | A61L 9/122 |
| 2018/0161471 | A1* | 6/2018 | Davis | A61L 9/127 |
| 2018/0335228 | A1* | 11/2018 | Brown | F04D 29/403 |
| 2019/0105458 | A1* | 4/2019 | Hammes | A61L 9/122 |
| 2020/0038541 | A1* | 2/2020 | Sharma | F24F 11/58 |
| 2020/0254130 | A1* | 8/2020 | Nixon | B60H 3/0007 |
| 2020/0254851 | A1* | 8/2020 | Nixon | B05B 12/02 |
| 2021/0213151 | A1* | 7/2021 | Amaral | A01M 1/2033 |
| 2021/0222896 | A1* | 7/2021 | Llorente Alonso | F24F 1/0355 |
| 2022/0133937 | A1* | 5/2022 | Lee | A61L 9/03 422/123 |

FOREIGN PATENT DOCUMENTS

| | | | | |
|---|---|---|---|---|
| KR | 20050011056 | A | * | 1/2005 |
| KR | 101691786 | B1 | * | 1/2017 |
| KR | 102009167 | B1 | * | 8/2019 |
| KR | 200490315 | Y1 | * | 10/2019 |
| KR | 20200065435 | A | * | 6/2020 |
| KR | 20210121964 | A | * | 10/2021 |
| WO | 01/51169 | A1 | | 7/2001 |
| WO | WO-2005079875 | A1 | * | 9/2005 ......... A01M 1/2033 |
| WO | 2006/058370 | A1 | | 6/2006 |
| WO | WO-2008124959 | A1 | * | 10/2008 ............ A61L 9/122 |
| WO | WO-2015040870 | A1 | * | 3/2015 ............ A61L 9/014 |
| WO | 2017/053979 | A1 | | 3/2017 |
| WO | WO-2019166114 | A1 | * | 9/2019 ............ A61L 9/122 |

* cited by examiner

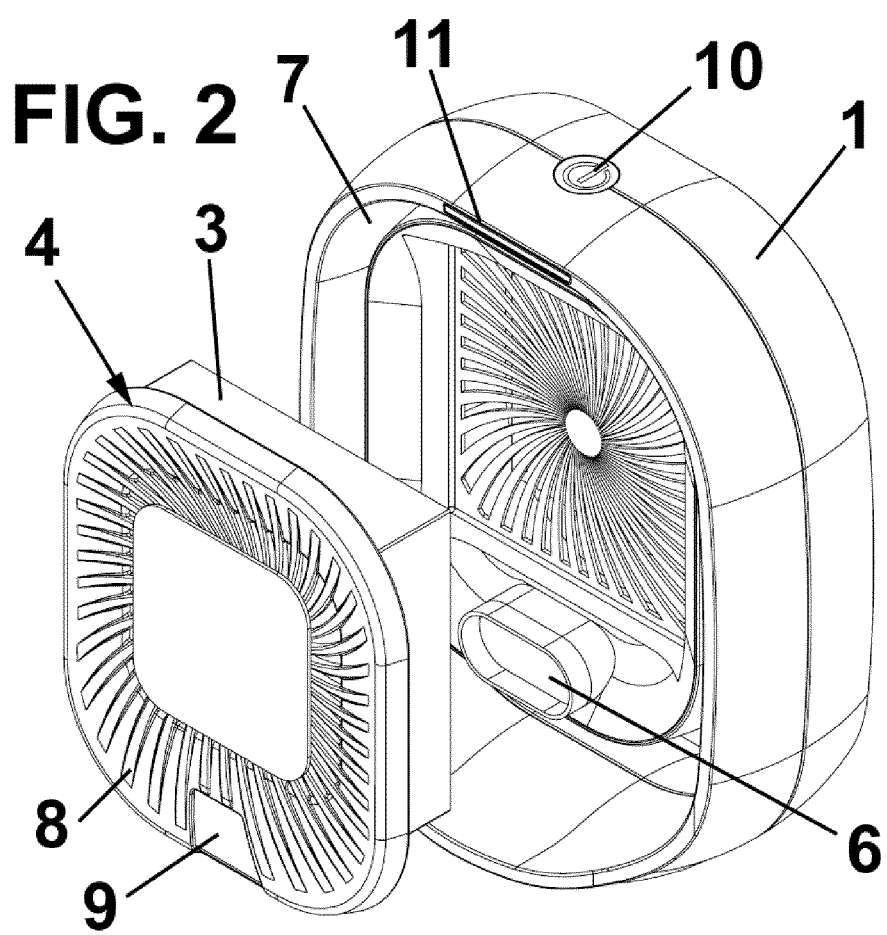

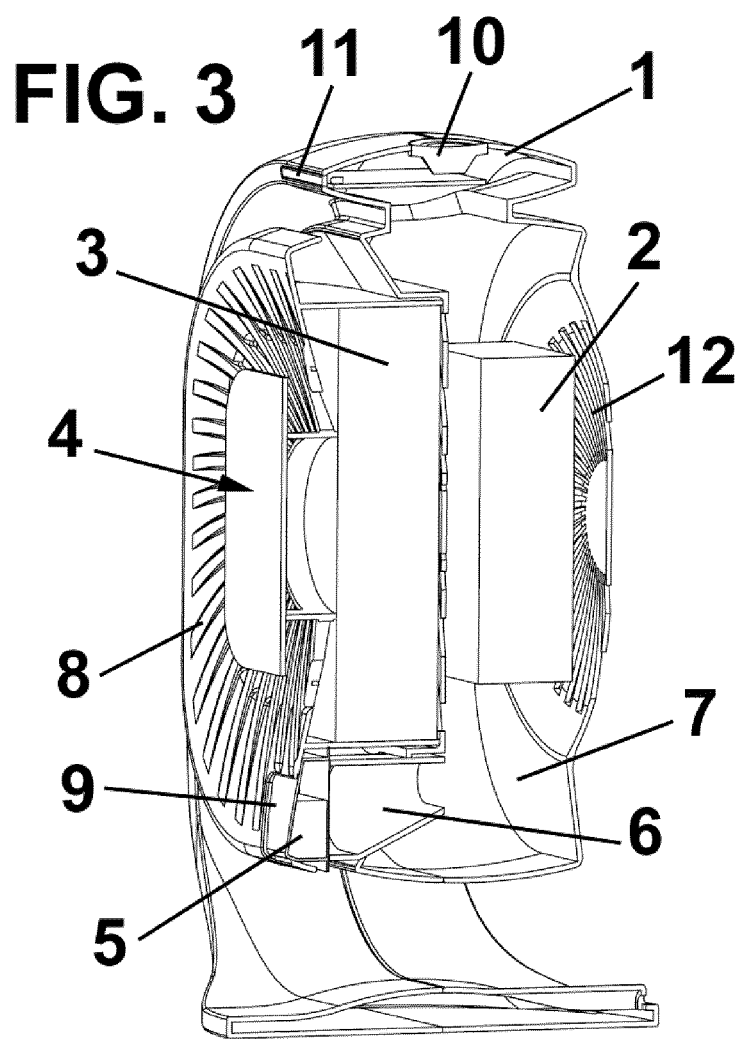

AIR PURIFICATION DEVICE

CROSS-REFERENCE TO RELATED APPLICATIONS

This application is a U.S. national stage entry under 35 U.S.C. § 371 of PCT International Patent Application No. PCT/EP2019/064973, filed Jun. 7, 2019, which claims priority to Spanish Patent Application No. P201830555, filed Jun. 7, 2018, the contents of each of which are incorporated herein by reference in their entirety.

The present invention relates to an air purification device that also allows for the diffusion of volatile substances.

BACKGROUND OF THE INVENTION

The purification of air in rooms by means of devices comprising filters through which air that is purified passes is common. In these devices, the air is moved through the filter by means of a fan between an inlet grill and outlet grill.

These conventional air purification devices fulfil their objectives to a greater or lesser degree, but they only purify air, without diffusing volatile substances, in other words, without emitting fragrance or insecticide.

Furthermore, another drawback of currently known air purification devices is that they can lose part of their filtering capability over time, if the filter is not replaced at the proper time.

Thus, one objective of the present invention is to provide an air purification device that allows for the purification of air and the diffusion of volatile substances at the same time.

DESCRIPTION OF THE INVENTION

The mentioned drawbacks are resolved with the air purification device of the invention, and other advantages are provided which will be described below.

The air purification device according to the present invention comprises a casing that houses a fan and a filter placed in front of said fan, such that air passes through said filter and exits the casing by means of said fan, and is characterised in that said filter is placed in a replaceable part mounted in a detachable way in said casing, said replaceable part comprising material with volatile substances.

Thanks to this feature, an air purification device is achieved that guarantees proper air purification, due to the fact that it guarantees a filter change when necessary, given that the same is integrated in the replaceable part. Furthermore, it allows the filtered air to mix with volatile substances that have an air-freshening and/or insecticidal effect.

Advantageously, said casing comprises an inlet for volatile substances into said fan.

Furthermore, said casing comprises a chamber for said volatile substances, placed around said fan, for example.

Advantageously, said filter is a filter with multiple layers that filters particles and gases.

According to a preferred embodiment, said replaceable part comprises an air inlet grill, and can also comprise a window in order to see the amount of material with volatile substances remaining in the replaceable part.

Moreover, said casing preferably comprises a single push button for turning on the device, turning off the device and selecting the operating mode, and an air purification percentage indicator.

Said casing can further comprise a replaceable part presence detector, wherein said detector prevents the device from turning on if it does not detect the presence of the replaceable part.

The inlet for volatile substances into the fan is preferably independent from said filter.

BRIEF DESCRIPTION OF THE DRAWINGS

To better understand what has been set forth, several drawings are attached in which a practical embodiment is schematically depicted merely by way of non-limiting example.

FIG. 2 is a perspective view of the air purification device according to the present invention, with the replaceable part removed; and FIG. 3 is a cross-sectional perspective view of the air purification device according to the present invention, with the replaceable part in the position of use.

DESCRIPTION OF A PREFERRED EMBODIMENT

Figure 1:
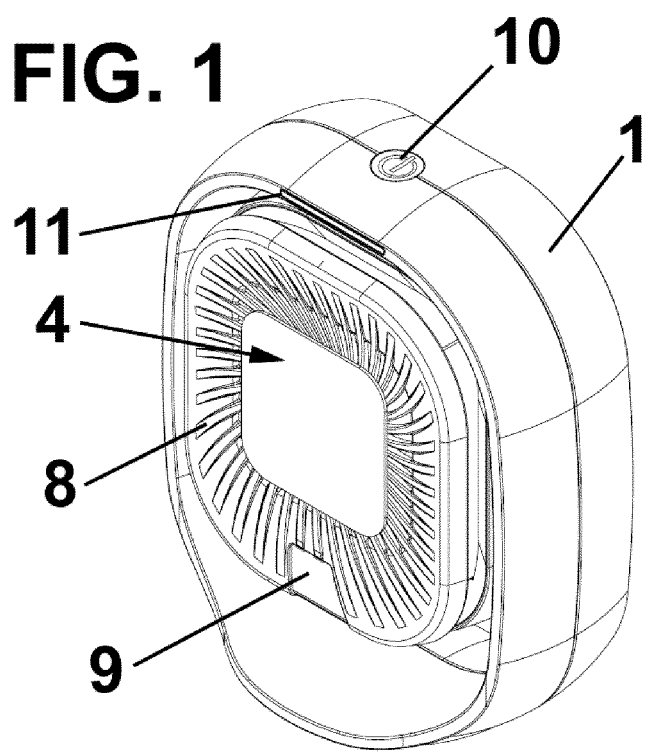
FIG. 1 is a perspective view of the air purification device according to the present invention, with the replaceable part in the position of use.

As shown in the figures, the air purification device according to the present invention comprises a casing 1 to which a replaceable part 4 is coupled in a detachable way.

Said casing 1 comprises a fan 2 that makes air circulate between an inlet grill 8, situated in the replaceable part 4, and an outlet grill 12, which can be seen in FIG. 3.

Said replaceable part 4 comprises a filter 3, specifically a filter with multiple layers to filter particles and gases, and a material with volatile substances 5, said volatile substances being fragrances or insecticides.

Moreover, the casing 1 further comprises an inlet 6 for the volatile substances into said fan 2 and a chamber 7 situated around said fan 2 where the purified air is mixed with the volatile substances.

Preferably, the filter 3 and the inlet 6 for volatile substances are in independent channels, the filter 3 being in the main axis of the flow and the volatile substances in a secondary channel with access to said chamber 7, where they mix with the filtered air. In other words, the main flow is focused on filtering the air.

The operation of the air purification device according to the present invention is the following:

When a user wants to use the device, they must first place a replaceable part 4 in the position of use, as shown in FIGS. 1 and 3. If the replaceable part 4 is not placed in the position of use, the device will not function, since it comprises a presence detector (not shown in the figures), such as a switch that is actuated by the replaceable part 4.

In the position of use of the replaceable part, the filter 3 is placed in front of the fan 2, as shown in FIG. 3.

If the presence of the replaceable part 4 is detected, by the actuation of the switch, for example, the user can turn on the device, by actuating a push button 10, for example, which can be placed on the upper part of said casing 1.

During the use of the device, the user can change the operating mode of the device, also by means of said push button 10, by quickly pressing said push button 10 one or two times, for example.

The purification device according to the present invention can further comprise an indicator 11 indicating the cleanliness percentage. For example, the indicator 11 can be a plurality of lights, such as five lights, each one indicating 20% of the volume of the room in which the air is to be purified.

To this end, the device itself will preferably indicate the surface area of the room for which the use of the device is intended, such that by calculating the flow coming out of the device, one can calculate the cleanliness percentage.

The air of the room enters the device through the inlet grill 8 and passes through the filter 3 to the fan. In turn, the volatile substances 5 of the replaceable part 4 pass to the chamber 7 by means of the inlet 6. This way, the purified air and the volatile substances mix and exit the outlet grill 12, actuated by the fan 2.

In order for the user to know the amount of material with volatile substances in the replaceable part 4 at all times, the same comprises a window 9. Given that the material with volatile substances is a bright colour, the user will be able to easily see the amount remaining in the replaceable part 4 through the window 9.

Once all of the material with volatile substances has been consumed, the user removes the worn replaceable part 4 and substitutes it with a new replaceable part 4, which also comprises a new filter 3, such that proper operation of the air purification device according to the present invention is always guaranteed.

Despite having referred to a specific embodiment of the invention, it is evident for one skilled in the art that the air purification device that has been described is susceptible to a number of variations and modifications, and that all the mentioned details can be replaced with other technically equivalent ones without departing from the scope of protection defined by the attached the claims.

The invention claimed is:

1. An air purification device comprising a casing (1) that houses a fan (2) and a filter (3) placed in front of said fan (2), such that air passes through said filter (3) and exits the casing (1) by means of said fan (2), wherein in that said filter (3) is placed in a replaceable part (4) mounted in a detachable way in said casing (1), said replaceable part (4) comprising material with volatile substances (5), and said casing (1) comprises an inlet (6) for providing volatile substances into said fan (2) and a chamber (7) for said volatile substances;

wherein the filter (3) and inlet (6) are provided in independent channels, wherein the filter (3) is positioned in a main axis of flow with the fan (2) to provide filtered air and the inlet (6) is provided in a secondary channel, independent of the main axis of flow, and in communication with the chamber (7) to provide volatile substance to be mixed with the filtered air.

2. The air purification device according to claim 1, wherein said chamber (7) is placed around said fan (2).

3. The air purification device according to claim 1, wherein said filter (3) is a filter with multiple layers that filters particles and gases.

4. The air purification device according to claim 1, wherein said replaceable part (4) comprises a grill (8) for the entry of air.

5. The air purification device according to claim 1, wherein said replaceable part (4) comprises a window (9) to be able to see the material with volatile substances (5) that remains in the replaceable part (4).

6. The air purification device according to claim 1, wherein said casing (1) comprises a single push button (10) for turning on the device, turning off the device and selecting the operating mode.

7. The air purification device according to claim 1, wherein said replaceable part (1) comprises an air purification percentage indicator (11).

8. The air purification device according to claim 1, wherein said casing (1) comprises a replaceable part presence detector (4), wherein said detector prevents the device from turning on if it does not detect the presence of the replaceable part (4).

9. The air purification device according to claim 1, wherein the inlet (6) for volatile substances into the fan (2) is independent from said filter (3).

10. The air purification device according to claim 1, wherein said casing (1) comprises a chamber (7) for said volatile substances.

11. The air purification device according to claim 10, wherein said chamber (7) is placed around said fan (2).

\* \* \* \* \*